United States Patent [19]

Jalowayski

[11] Patent Number: 4,800,896
[45] Date of Patent: Jan. 31, 1989

[54] CELL SAMPLE COLLECTOR PROBE

[76] Inventor: Alfredo A. Jalowayski, 6864 Lipmann Street, San Diego, Calif. 92122

[21] Appl. No.: 928,860

[22] Filed: Nov. 10, 1986

Related U.S. Application Data

[63] Continuation-in-part of Ser. No. 796,186, Nov. 8, 1985, abandoned, which is a continuation of Ser. No. 421,822, Sep. 23, 1982, abandoned.

[51] Int. Cl.$^4$ ............................................. A61B 17/22
[52] U.S. Cl. ..................................... 128/759; 128/304
[58] Field of Search ............... 128/757, 759, 304, 778, 128/396, 397, 398

[56] References Cited

U.S. PATENT DOCUMENTS

| | | | |
|---|---|---|---|
| 839,461 | 12/1906 | Reavley | 128/304 |
| 3,110,304 | 11/1963 | Hartman | 128/304 |
| 3,929,138 | 12/1975 | Curi | 128/304 |
| 3,955,579 | 5/1976 | Bridgman | 128/304 |
| 4,121,572 | 10/1978 | Kazeninski | 128/778 |

OTHER PUBLICATIONS

Richard's Manufacturing Catalog © 1966.

Primary Examiner—Edward M. Coven
Attorney, Agent, or Firm—Fulwider, Patton, Rieber, Lee & Utecht

[57] ABSTRACT

An elongated plastic sample collector probe for cell sampling, particularly including mucosal cells. The probe has a generally rigid rearward handle portion, a forwardly narrowing tapered shank portion, and a small sample collector cup at the forward tip of the shank portion. The plastic material of which the probe is made has the physical characteristics of flexibility and elasticity, and these characteristics cooperate with the forwardly narrowing taper to provide the probe with a progressively increasing transverse flexibility toward the collector cup. Such flexibility, together with the configuration and orientation of the cup relative to the shank portion, facilitates cell sample collection through use of a light, whisking stroke, which minimizes the likelihood of injury to sensitive tissues. In one form of the invention the probe is made of a light-conducting plastic material and a rearward part of the probe is coupled with an illuminating unit for transmission of light forwardly through the shank portion to the sample collecting cup at the forward tip so as to illuminate the cup and the sample collecting region.

8 Claims, 2 Drawing Sheets

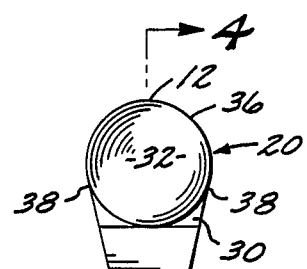
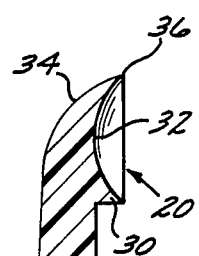

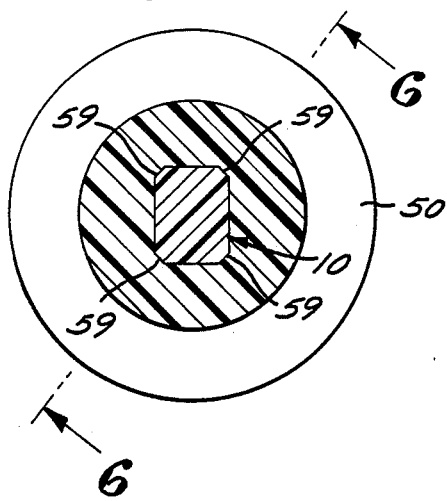
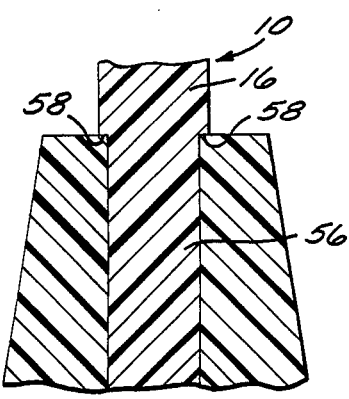
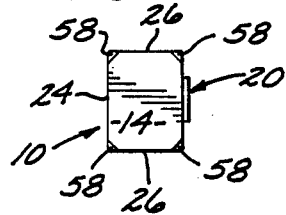
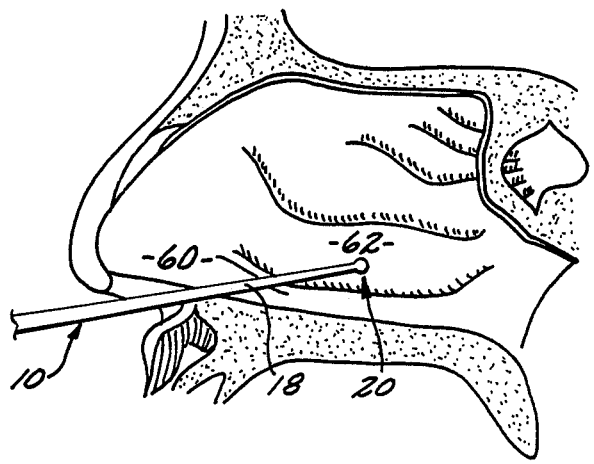
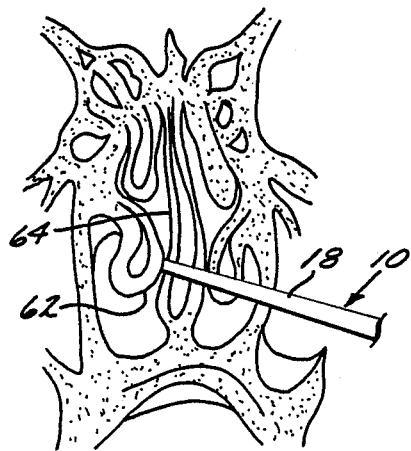
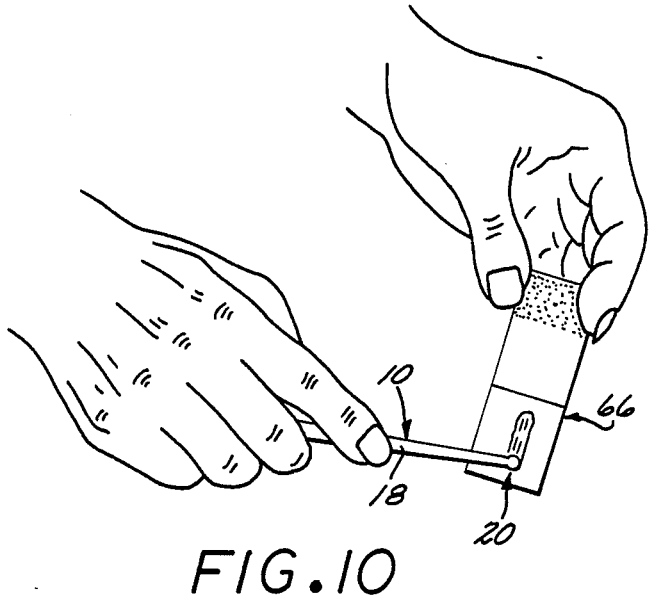

CELL SAMPLE COLLECTOR PROBE

CROSS REFERENCE TO RELATED APPLICATION

This application is a continuation-in-part of Ser. No. 796,186, filed Nov. 8, 1985, abandoned, which is a continuation of Ser. No. 421,822, filed Sept. 23, 1982, abandoned.

BACKGROUND OF THE INVENTION

1. Field of the Invention

The present invention is in the field of medical instruments, and it relates particularly to an instrument for safely and gently collecting a cell sample, transporting such sample from the collection site to an inspection site.

2. Description of the Prior Art

For the diagnosis of various human and animal disorders it is important to obtain adequate cell samples for inspection. Typical instances include diagnosis of allergic and infectious eye and nasal problems, rectal infections, herpes infections, vaginal infections, chlamydia, and viral diseases, particularly viral diseases whose diagnosis involves the use of monoclonal or polyclonal antibodies. For example, in diagnosing an allergic condition or a nasal infection, the conventional prior art procedure is to employ a wire loop with a cotton tip, working the cotton tip up and down against mucosa or mucous membrane tissue in an endeavor to get cells to adhere to the cotton so as to obtain a sample of the tissue. The preferred sites from which such a mucosa sample was to be obtained was one of the inferior turbinates, and the clearance between the inferior turbinates and the septum is so narrow (only about 1 mm) that the conventional cotton-tipped wire loop implement was difficult to manipulate in the constricted space. Thus, in many instances it was not possible with this conventional implement to obtain a good enough sample for analysis of the diseased mucosa tissue.

A mucosa sample from the constricted region of one of the inferior turbinates would be much more reliably obtainable by the use of a medical instrument capable of scraping up the tissue sample instead of having to attempt to rub cells off of the tissue by means of a cotton-tipped implement. However, no such medical instrument has been available prior to the present invention, apparently because of the delicacy and vulnerability to injury of the tissue, and also the space constriction in the region from which the tissue sample must be taken. The prior art medical instruments which come closest in appearance to the present invention are curettes, which are metal instruments that are used for scraping bones of the ear, and which for such function are required to be generally rigid. Such metal instruments are much too dangerous to introduce into the nasal cavity because of the likelihood of injury, particularly in the case of children who tend to move around under the stress of such medical attention. In addition, use of metal instruments is unsuitable in several applications since the metal can be toxic either to the organism or to the cell culture with which the probe will come in contact. Examples of such generally rigid metal curettes are disclosed in Russian Patent No. 219,091, German patent No. 362,997, and U.S. Pat. No. 839,641. Other medically related implements which bear some limited resemblance to the present invention include a double-ended metal rod structure having small spoon-shaped cavities at both ends for obtaining secretion samples from the urethra and cervix disclosed in U.S. Pat. No. 1,669,395; a rigid plastic ear spatula device having an enlarged handle which tapers down in a narrowing shank contoured to fit the ear canal, and then enlarges to a cupped forward tip shown in U.S. Pat. No. 2,425,917; and a dissector for stripping thickened intima in sclerotically diseased arteries, the instrument being made of metal, having an enlarged handle, a long thin shaft of uniform thickness made of a malleable metal having limited resiliency and flexibility and being bendable to retain a bent configuration, and an enlarged trowel-like operational tip, disclosed in U.S. Pat. No. 3,929,138.

In the above-referenced German Patent No. 362,997, the curette is longitudinally adjustable relative to its handle, and indexing lines on the shaft indicate how far forward the operative tip of the curette is from a stop flange associated with the handle.

None of these prior art medical instruments would be suitable for use in obtaining cell samples such as nasal mucosa samples.

SUMMARY OF THE INVENTION

In view of these and other problems in the art, it is a general object of the present invention to provide a cell sample collector probe which is suitable for obtaining a small scraping of cell samples from human or animal sites of suspected infections and diseases. A particular application which is specifically discussed in this disclosure is the collection of cell samples from mucosa tissue from the nasal cavity. However, the structure and arrangement of the probe adapts it to cell sample collection in many other applications which presently exist or which may hereafter develop.

Another object of the invention is to provide a cell sample collector probe which is capable of reliably collecting cell samples, yet which is delicate and gentle in operation, and not likely to cause injury to the patient.

Another object of the invention is to provide a cell sample collector probe which, in one embodiment, is made of a plastic material having physical characteristics of flexibility and elasticity which cooperate with a tapered configuration to provide a progressively increasing flexibility of the probe shank approaching the forward, operative tip of the probe, providing the probe with its delicate, gentle and safe characteristics for use in obtaining a superficial mucosal sample.

A further object of the invention is to provide a cell sample collector probe of the character described which in one form is composed of a light-conducting plastic material, and a light source connectable to the the rear end of the probe to direct light longitudinally through the probe which is emitted from forward portions of the probe to illuminate the operative tip of the probe as well as the region from which the cell sample is to be secured.

A still further object of the invention is to provide a form of the cell sample collector probe of the character described which has a series of regularly spaced indexing marks or lines along its shank to assist in the repeatable location of a particular cell sample collection site.

Yet a further object of the invention is to provide a small, unitary cell sample collector probe which is economical to manufacture and suitable to be merchandised as a throw-away device, thereby eliminating the necessity for sterilizing the device after use.

Another object is to provide a cell sample collector probe of the character described which has a collector cup at its forward tip that is offset above the adjacent shank of the probe, which facilitates the transfer of cell samples onto a microscope slide.

The preferred form of the cell sample collector probe of the invention is an elongated, unitary plastic device having a rearward handle portion, a shank portion that continuously narrowingly tapers forwardly from the handle portion, and a tiny collector cup rigidly formed at the forward end of the shank portion. The plastic material of which the probe is made has the physical characteristics of being flexible and elastic, and these characteristics cooperate with the relatively large cross-section of the handle and the continuous but narrowing taper forward to the collector cup to provide a generally rigid rearward portion of the probe and a progressively increasing flexibility of the shank portion of the probe approaching the forward tip, whereby manipulation of the forward tip of the probe from the handle portion can be sure and positive, and while sufficient lateral force can be imparted from the handle portion to the collector cup at the forward tip to employ a gentle wiping or whisking type of scraping action for collecting a mucosa sample; nevertheless the forward portion of the probe is so flexible as to not be likely to cause damage to delicate tissues.

The forward part of the shank and the collector cup at its tip are so tiny in cross-sectional dimension as to be adapted in nasal mucosa cell collection for insertion into the tightly constricted space between one of the inferior turbinates and the septum for collecting a sample off of the inferior turbinate. The front edge of the collector cup is a sharp edge for scraping up the mucosa sample in a withdrawing or outward wiping motion. The upper edge of the collector cup is offset upwardly from the adjacent upper surface of the shank portion to make transfer of a collected sample to a microscope slide a simple and reliable operation.

One aspect of the invention is the coupling of a light-conducting form of the nasal or vaginal sample collector probe with an illuminating unit which provides light from the rearward end of the probe through the shank of the probe to the sample collecting cup at the forward tip for illuminating the cup and the sample collecting region.

Other aspects and advantages of the present invention will become apparent from the following more detailed description taken in conjunction with the accompanying drawings.

BRIEF DESCRIPTION OF THE DRAWINGS

FIG. 1 is a perspective view showing a cell sample collector probe according to the invention operatively associated with an illuminating unit;

FIG. 2 is a side elevational view of the apparatus shown in FIG. 1, with portions shown in axial section, and with portions broken away;

FIG. 3 is a greatly enlarged, fragmentary top plan view showing the forward end portion of the probe;

FIG. 4 is an axial section taken on the line 4—4 in FIG. 3;

FIG. 5 is an enlarged cross-sectional view taken on the line 5—5 in FIG. 2;

FIG. 6 is a fragmentary axial section taken on the line 6—6 in FIG. 5;

FIG. 7 is a rear end view of the probe;

FIG. 8 is a fragmentary sectional view, with portions shown in elevation, illustrating the probe of the invention operatively located in the nasal cavity, looking toward one side of the nasal cavity;

FIG. 9 is another fragmentary sectional view, with portions shown in elevation, illustrating the probe operatively positioned in the nasal cavity looking rearwardly into the nasal cavity; and FIG. 10 is a perspective view illustrating the transfer of a nasal mucosa sample from the probe of the invention to a microscope slide.

DESCRIPTION OF THE PREFERRED EMBODIMENT

Referring now to the drawings, and at first particularly to FIGS. 1–4 thereof, the cell sample collector probe of the present invention is generally designated 10, and is of elongated, slender, unitary construction having a front end 12 and a rear end 14. Along the length of the probe from rear end 14 to front end 12 there is a rearward handle portion 16 of substantially uniform cross-section which preferably extends approximately one-third the length of the probe 10, and a forward tapered shank portion 18 which terminates at its forward tip in a tiny collector cup generally designated 20 which serves the functions of scraping up a cell sample from a collection site. In the application herein described, the cell sample is a mucosa cell sample from the nasal cavity, which is transferred to a microscope slide for inspection. However, the invention comprehends the collection of cell samples from other sites of infection or disease for analysis or inspection by means of any of a variety of diagnostic systems available in the medical profession. Accordingly, reference to mucosa cell sample collection is by way of example and not by way of limitation.

In the following description the terms "upper" and "lower" have been arbitrarily chosen in order to facilitate and clarify the description, and it is to be understood that these terms have not been used by way of limitation.

The probe 10 preferably has a generally rectangular cross-sectional configuration from its rear end 14 forwardly up to the collector cup 20. This generally rectangular cross-section is defined within generally flat surfaces including an upper laterally directed surface 22, a lower or oppositely laterally directed surface 24, and a pair of side surfaces 26.

A series of regularly spaced, transverse indexing lines 27 is disposed along approximately the forward half of the length of probe 10 to assist the operator in returning to the same collection site at a later time for collecting another sample. The indexing lines 27 preferably designate longitudinal increments of one cm, and the indexing lines 27 are preferably formed as shallow grooves across the upper surface 22, although they may alternatively be shallow ribs or imprinted lines.

The longitudinal point along the length of probe 10 at which the taper of the tapered shank portion 18 begins is generally designated 28. Along the entire length of the tapered shank portion 18 the probe 10 is wider between the side surfaces 26 (the width direction) than it is thick between the upper and lower surfaces 22 and 24, respectively (the thickness direction). This is for two purposes: (1) maximum flexibility of a continuously increasing extent toward the forward tip of the probe is required in the thickness direction to avoid injury to the patient, inasmuch as it is the thickness direction in which the slight scraping force is applied during sample collection, the somewhat greater width than thickness along the entire length of the taper providing the necessary structural strength along with a required amount of flexibility in the width direction to avoid injury to the patient; (2) generally the mucosa sample will be collected from the inferior turbinate, and there is only approximately one mm of clearance between the septum and each of the inferior turbinates; this requires that the tapered shank portion 18 of the probe be as thin as possible between the upper and lower surfaces 22 and 24, respectively, approaching the forward tip 12 of the probe.

The tapered shank portion 18 of the probe tapers continuously and preferably at a uniform rate of taper from its beginning point 28 forwardly all the way to the collector cup 20. The material of which the probe 10 is made has the requisite characteristics of both flexibility and elasticity. These essential characteristics of the material cooperate with the continuous and preferably uniform taper to provide a progressively increasing flexibility and resiliency of the probe 10 right up to the forward tip 12 to enable the necessary small amount of force to be applied at the collector cup 20 for scraping up a mucosa sample, while at the same time providing assurance against injury to the delicate nasal tissues. This elastic flexibility of the tapered shank portion 18 approaching the forward tip 12 of the probe is so delicate and refined that the most a patient will normally feel during the collection of a mucosa sample is a feather-like whisk.

The material of which the probe 10 is made that has these essential characteristics of flexibility and elasticity is preferably a plastic material such as an acrylic or "plexiglass". It is preferred that this plastic material have good light conducting characteristics for use of the probe 10 with a light source as shown in FIGS. 1, 2, and 5-7, and as described in detail hereinafter. Plexiglass is an example of a material having the desired light conducting characteristics. The use of such plastic materials enables the probe 10 to be very economically manufactured so that it may be marketed as a disposable device, and the delays and other inefficiencies associated with sterilization by autoclaving may be avoided.

Even if the probe 10 of the invention is not intended for use in combination with a light source as shown in FIGS. 1, 2 and 5-7, it is preferred that the collector cup 20 at the forward tip of the probe be generally transparent to facilitate visual observation by the user of the probe that a satisfactory sample has been collected.

The collector cup 20 is rigidly associated with the front end of the tapered shank portion 18, and is formed by a rigid wall means or platform 30 that is displaced laterally outwardly of the upper surface 22 of the probe. The cup 20 thus projects laterally outwardly to define a concave cavity or surface 32 opening laterally outwardly, but otherwise closed. The surface 32 is preferably generally smooth and spherical in contour, as illustrated.

The cup 20 has a generally upwardly and forwardly facing convex, rounded outer surface 34 that is formed as a continuation of the lower surface 24 of the probe. This convex outer surface 34 intersects the concave cavity or inner surface 32 at a sharp forward scraping edge or lip 36 that preferably extends around at least approximately the front 180 degrees of the cup 20, and preferably somewhat more than 180 degrees. This sharp forward lip 36 of the cup 20 is best seen in FIGS. 3 and 4, and as seen in FIG. 3 the sharp lip 36 is peripherally continuous.

The cross-sectional size of the probe 10, particularly in the tapered shank portion 18 approaching the front end 12 of the probe, is an important aspect of the invention both for utilization of the flexibility and elasticity characteristics of the plastic material and for obtaining access to the tightly constricted nasal zone from which the mucosa sample is to be obtained. At the same time, the cross-sectional size in the rearward handle portion 16 is preferably sufficient so that this portion of the probe 10 is generally rigid and of a comfortable size to be gripped between the fingers of the person using the probe. An example of the invention which has proven to be completely satisfactory in operation has the following approximate dimensions: it has an overall length of approximately 10 cm, approximately one-third of which is the rearward handle portion 16 and two-thirds of which is the tapered shank portion 18. The handle portion 16 is approximately 4—½ mm wide by approximately 3—⅜ mm thick. The shank portion 18 tapers from these cross-sectional dimensions continuously and at a uniform rate down to minimum cross-sectional dimensions proximate the collector cup 20 of approximately 1.3 mm wide by approximately 0.9 mm thick. Thus, the rate of taper along the length of the tapered shank portion 18 is slightly greater in the width direction than in the thickness direction, and in both of these directions is within a range of between about 0.4 and 0.5 mm per cm.

The overall diameter of the collector cup 20 of the example of probe 10 described in the preceding paragraph is approximately 2 mm, and the upper edge of the cup 20 defined by the raised platform 30 is displaced approximately one-half mm above the upper surface 22 of the probe. The very small dimensions of the collector cup 20 combined with its structural shape make the cup 20 rigid, which is desirable for its scraping function.

The offset or raised level of cup 20 above, i.e. laterally outwardly of, the upper surface 22 of the probe facilitates deposition of a cell sample onto the flat surface of a microscope slide in a wiping type of action, by avoiding interference from the adjacent shank portion 18 of the probe. The periphery of the collector cup 20 preferably lies in a plane that is substantially parallel to the plane of the upper surface 22 of the probe, as seen in FIG. 4. This facilitates both the taking of a sample and the wiping of the sample onto a microscope slide, because the user of the probe then knows the exact orientation of the cup 20 by feel of the probe 10 in his hand, without having to attempt to look at the operative upper face of the cup 20 which is not only difficult to see because of its very small size, but is directed generally away from the user's vision during both the sample collecting and microscope depositing operations. As a further refinement to this orientation by feel, it is preferred to have the entire upper surface 22 along the length of the probe 10 flat, and to provide the taper in the thickness direction by inclining the part of lower surface 24 that registers with the tapered shank portion 18 upwardly relative to the part of lower surface 24 that registers with the rearward handle portion 16.

Another aspect of the configuration of probe 10 that is useful in the proper orientation of the probe by feel is the rectangular cross-sectional shape of the probe, with the flat upper and lower surfaces 22 and 24, respectively, of the rearward handle portion 16 being oriented parallel to the upper edge of the cup 20, and the side surfaces 26 of the rearward handle portion 16 being oriented at right angles to the upper edge of the cup 20. This allows either the upper and lower surfaces or the side surfaces of the handle portion 16 to be gripped between opposing fingers, with the user knowing by feel what the orientation of the upper edge of the cup 20 is.

FIGS. 1, 2 and 5-7 illustrate the optional use of a transparent, light-conducting probe 10 in combination with a small battery-powered pen light generally designated 40 which serves both as a light source and as an enlarged handle for the probe 10. The pen light 40 has a generally cylindrical casing 42 which contains one or more batteries that may be either replaceable or rechargeable. A light bulb 44 is axially centered at the front end of casing 42, and a pocket clip type switch 46 is rearwardly disposed along the side of casing 42. An insulation sleeve 48 is axially slidably engaged over the cylindrical casing 42 and is axially shiftable between a rearward "off" position shown in FIG. 1 in which it is interposed between the clip 46 and switch contacts 49, and a forward position forward of the clip 46 which enables the clip 46 to spring radially inwardly against contacts 49 to close the contacts and turn the light bulb on. The insulation sleeve 48 may the be shifted rearwardly to engage over the forward end portion of clip 46 as shown in FIG. 2 to secure the switch in its "on" position.

A probe mounting collar 50 made of resilient elasomeric material has a rearwardly opening cylindrical recess 52 that enables collar 50 to be frictionally engaged over the forward end portion of cylindrical casing 42. Mounting collar 50 has an axial passage 54 extending therethrough, the passage 54 having a rectangular cross-sectional configuration that generally registers with the rectangular cross-section of the rearward handle portion 16 of probe 10, but is somewhat smaller for frictional engagement of the probe handle 16 therein. If the probe 10 is to be adapted for use in connection with a pen light 40, it is preferred that the handle portion 16 of the probe have a rear mounting section 56 which has rearwardly facing corner stop shoulders 58 provided by bevels 59 on the four corners as shown in FIGS. 5-7. This assists proper locating of the rear end portion of the probe 10 in the mounting collar 50 by engagement of the stop shoulders 58 against the forward surface of mounting collar 50 when the rear end portion of probe 10 is pushed down into the axial passage 54 of mounting collar 50.

In operation, with the light bulb 44 turned on, light is emitted from all four surfaces along the length of the tapered shank portion 18 of probe 10, such emission appearing to increase in amplitude as the probe becomes thinner and thinner toward the front end 12 thereof, with the collector cup 20 being brightly illuminated. This provides excellent lighting within the nasal cavity, and particularly proximate the cup 20 to facilitate the membrane scraping operation.

If the illuminator pen light 40 is not employed with the probe 10 to provide the direct internal illumination referred to above within the nasal cavity, then illumination must be provided by some external source such as a bi-valve nasal illuminator held by one hand while the probe is manipulated by the other hand, or a light-reflective mirror mounted on the forehead of the user. In any case, the entrance to the nasal passages must be opened by some form of speculum to provide convenient visual and mechanical access, and the sample collection site must be illuminated.

Operation of the nasal sample collector probe 10 is generally illustrated in FIGS. 8, 9 and 10. The forward part of the tapered shank portion 18 of the probe is inserted through the nasal vestibule 60 as best seen in FIG. 8, with the concave upper surface 32 of the collector cup 20 facing toward an inferior turbinate 62. The cup 20 and a forward section of the tapered shank 18 will, in this position of the probe 10, be inserted in the very narrow space between the inferior turbinate 62 and the septum 64 as shown in FIG. 9. Then, the concave upper surface 32 of the collector cup 20 is gently pressed on the mucosal surface of the inferior turbinate 62 and the sample is quickly collected with a short (2 to 3mm) outward or withdrawing scraping movement of the collector cup 20 against the inferior turbinate 62. The tip of the probe 10 is then gently withdrawn from the nasal cavity, avoiding any touching of the upper surface 32 of cup 20 against the anterior surface of the nose to avoid contamination of the sample that has been collected.

Then, the contents of the collector cup 20 of the probe are spread on a microscope slide 66 in the manner illustrated in FIG. 10 by placing the sample-containing upper side of the cup 20 against the flat surface of the microscope slide 66 and applying gentle pressure to the flexible, resilient tapered shank 18 and moving the cup 20 a few mm across the surface of the slide. Then, the mucosa cells thus collected and applied to the microscope slide 66 are analyzed by conventional means to diagnose a condition of allergy or infection. The probe 10 may then be discarded, and the next similar operation performed with a new, sterile probe 10.

While the invention has been described with reference to presently preferred embodiments and particularly those related to mucosa cell sample collection, it is to be understood that the invention is suited generally to cell sample collection from other sites in both humans and animals, and that various modifications and changes may be made with regard to the foregoing detailed description without departing from the spirit of the invention.

I claim:

1. A nasal mucosa sample collector probe which comprises:
   a generally rigid rearward handle portion;
   a elongated shank portion connected to and extending forwardly from said handle portion; and
   a sample collector cup generally rigidly connected to the forward end of said shank portion with the concavity of the cup facing generally transversely to the longitudinal direction of said shank portion;
   at least a forward part of said shank portion having as forwardly narrowing taper extending to said cup and being composed of a plastic material that is flexible and elastic so that said forward part of the shank portion has a progressively increasing transverse flexibility toward said cup which minimizes the likelihood of injury to sensitive nasal tissues, said forward part of said shank portion further being thinner and hence more flexible in said cup-facing transverse direction than in the transverse direction at right angles thereto.

2. A sample collector probe as defined in claim 1, wherein said handle portion, said shank portion and said cup are integrally formed of said plastic material.

3. A sample collector probe as defined in claim 1, wherein the greater length of said shank portion is substantially continuously tapered.

4. A sample collector probe as defined in claim 3, wherein the taper is substantially uniform along its length.

5. A sample collector probe as defined in claim 1, wherein said cup includes a scraping edge having a forward portion forming the forward terminus of the probe.

6. A sample collector probe as defined in claim 1, wherein said cup has a forward outer surface which is continuous.

7. A sample collector probe as defined in claim 1, wherein said handle portion extends approximately the rearward one-third of the length of the probe.

8. A sample collector probe as defined in claim 1, wherein said handle and shank portions have generally continuous, generally flat top, bottom and side surfaces defining rectangular cross sections of said handle and shank portions, and
 wherein both said handle and shank portions are thinner in cross section between said upper and lower surfaces than between said side surfaces.

* * * * *